United States Patent [19]

O'Brien

[11] Patent Number: 4,924,879
[45] Date of Patent: May 15, 1990

[54] BLOOD LANCET DEVICE

[76] Inventor: Walter J. O'Brien, 736 Scotch Plains Ave., Westfield, N.J. 07090

[21] Appl. No.: 254,860

[22] Filed: Oct. 7, 1988

[51] Int. Cl.$^5$ .............................................. A61B 5/00
[52] U.S. Cl. .................................. 128/770; 606/182; 606/185
[58] Field of Search ............... 128/314, 315, 329 R, 128/329 A, 330, 637, 638, 770; 604/22, 46, 47, 136, 156, 157; 606/167, 181, 182, 185, 189

[56] References Cited

U.S. PATENT DOCUMENTS

| | | | |
|---|---|---|---|
| 3,030,959 | 4/1962 | Grünert | 128/314 |
| 3,797,488 | 3/1974 | Hurschman et al. | 604/136 |
| 4,416,279 | 11/1983 | Lindner et al. | 128/770 |
| 4,442,836 | 4/1984 | Meinecke et al. | 128/314 |
| 4,469,110 | 9/1984 | Slama | 128/314 |
| 4,503,856 | 3/1985 | Cornell et al. | 128/314 |
| 4,527,561 | 9/1985 | Burns | 128/637 |
| 4,535,769 | 8/1985 | Burns | 128/637 |
| 4,539,988 | 10/1985 | Shirley et al. | 128/314 |
| 4,577,630 | 3/1986 | Nitzsche et al. | 128/314 |
| 4,616,649 | 10/1986 | Burns | 128/314 |
| 4,624,253 | 11/1986 | Burns | 128/314 |
| 4,627,445 | 12/1986 | Garcia et al. | 128/770 |
| 4,643,189 | 2/1987 | Mintz | 128/314 |
| 4,653,513 | 3/1987 | Dombrowski | 128/770 |
| 4,677,979 | 7/1987 | Burns | 128/314 |
| 4,735,203 | 4/1988 | Ryder et al. | 128/314 |

Primary Examiner—Randall L. Green
Assistant Examiner—Randy Shay
Attorney, Agent, or Firm—Alvin S. Blum

[57] ABSTRACT

A blood letting lancet assembly for puncturing the skin of the finger tip for home use that causes less pain includes a mechanism for reproducibly orienting the assembly on the finger tip. The blade may be moved to any of a plurality of indexed positions within the device. By indexing the blade to the next position and reproducibly orienting the device on the finger tip, the user can avoid a second puncture close to the first puncture which reduces pain. A new method for rapidly advancing and retracting the blade further reduces pain. An accessory capillary collects the exact volume of blood required for a test and avoids needless attempts to collect excessive blood. A magnetic blade holder simplifies blade changing.

41 Claims, 3 Drawing Sheets

BLOOD LANCET DEVICE

The present invention is concerned with blood letting devices and more particularly with finger pricking devices using disposable blades for repeated samplings of capillary blood for home use with minimal pain and injury to the patient.

In the treatment of diabetes with insulin, it is generally agreed that the serious complications of the disease are prevented or delayed by careful control of the blood sugar level. Effective control of the blood sugar level often requires monitoring or measuring the concentration of blood sugar by repeated samplings. There are simple blood sugar measuring devices for patient use that simply involve placing a small portion of blood on a thin membrane strip and comparing color developed to a standard chart. There are such problems with obtaining the small samples of blood that fewer than one-fifth of the diabetics routinely monitor their blood sugar. The result is that most diabetics fail to maintain their blood sugar levels within the range that will be most effective.

The biggest drawback to routinely drawing small blood samples is the pain inflicted by the currently available lancets or finger-sticking devices. The most favored site of sampling is the rich capillary bed of the skin of the finger tip which readily yields a drop of blood from a small cut. The finger tip is also rich in pain receptors, and the pain is increased when the incision is too deep, or is too close to a recent incision, or is not deep enough requiring an additional incision. Furthermore the pain may be increased if the cutting blade penetrates slowly or is withdrawn slowly. Furthermore, the user may be forced to make a larger incision than is necessary in order to get a drop of blood to form for transfer to the measuring strip.

SUMMARY OF THE INVENTION

It is, accordingly, an object of the invention to provide a blood letting device employing a replaceable and disposable blade with a stabbing or blade advancing and retracting means that carefully controls the depth of penetration and automatically advances and retracts the blade in a minimum of time for reduced pain.

It is a further object to provide the device as described that carefully locates the site of incision and ensures that subsequent incisions will be made at other locations on the finger tip.

It is yet another object of the invention to provide the device as described with a volumetric blood collecting means so that the user will be assured that the volume of blood necessary for the measurement has been collected in a form most convenient for measurement.

The blood lancet device of the invention comprises a finger positioning ring that fits on the fingertip with a locating arm that extends over the fingernail. An assembly carrier is rotatably attached to the end of the ring with a spring loaded detent with four click-stops so that the assembly carrier can be positioned to four different orientations. The locating arm on the finger positioning ring enables the user to position the device to the same location on the finger, and by rotating the assembly carrier to the next orientation, the incision is automatically made at a new site, thereby reducing discomfort. A lancet assembly fits within the assembly carrier. The lancet assembly has a blade holder for conveniently removing and installing disposable skin incising blades.

The blade holder has a blade advancing and retracting mechanism that is powered by a cocked spring. When a pushbutton is depressed, the mechanism advances the blade holder and blade a fixed distance and promptly retracts it in a very fast motion provided by a rotary to translatory mechanism. The lancet assembly moves axially within the assembly carrier, and a skin surface sensor at the end of the assembly positions the assembly a fixed distance above the skin surface so that the blade will penetrate a controlled depth through the skin regardless of the curvature of the finger tip or the click-stop position. The skin surface sensor may be adjustable to change the depth of penetration of the blade.

These and other objects, advantages and features of the invention will become more fully apparent when the following detailed description of the preferred embodiment of the invention is read in conjunction with the accompanying drawings.

DETAILED DESCRIPTION OF THE PREFERRED EMBODIMENT

Figure 1:
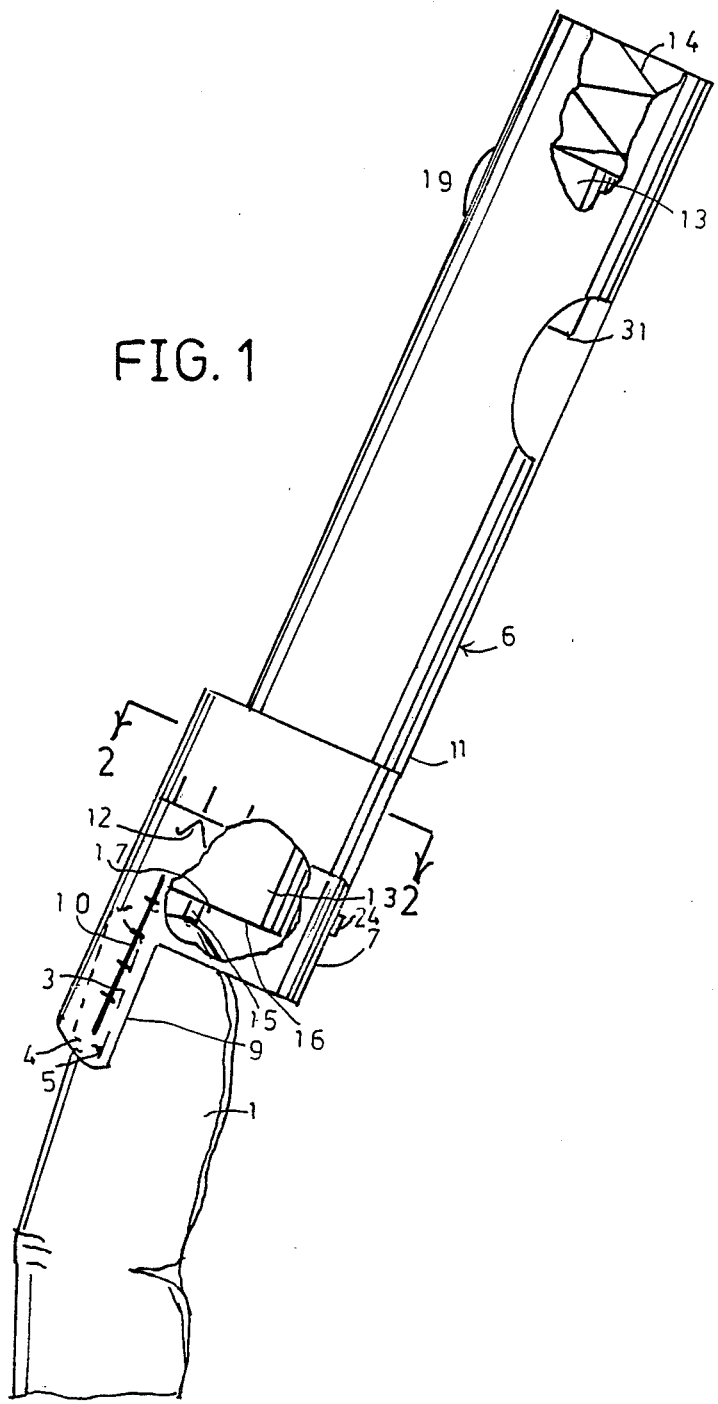
FIG. 1 is a side elevation of the device in place on a fingertip with portions broken away to show internal structure.

Referring now first to FIG. 1, an index position for reproducibly positioning the lancet device 6 on the finger 1 is the point 5 where the lateral edge 3 of the fingernail meets the cuticle 4. A transparent finger-positioning ring 7 has a locating arm 9 with markings 10 for reproducibly positioning the device 6 relative to finger 1 by always setting a mark 10 at the point 5. An assembly carrier 11 is rotatably attached to finger-positioning ring 7 with a spring loaded detent 12 providing four click stops much like the aperture settings on a camera so that assembly carrier 11 may be rotated to any one of four positions relative to the finger 1, as indicated by blades 36 shown in phantom in FIG. 2.

Within the assembly carrier 11 is the lancet assembly 13 that is axially slidable within the assembly carrier. A soft compression spring 14 gently urges the bottom 16 of lancet assembly 13 against the skin surface. A skin surface sensor 15 mounted on end 16 of the lancet assembly holds the lancet assembly and the blade a fixed distance above the skin surface. The sensor 15 is very close to the point of the lancet blade 17 so that the distance of the point above the skin surface is automatically set regardless of the curvature of the finger tip or the click-stop setting.

A pushbutton 19 on the side of the assembly carrier 11 fires the spring loaded blade 17 which rapidly moves downward below the bottom edge 16 of lancet assembly 13 a fixed distance and then retracts. The motion is very fast through a powerful spring to reduce pain.

Figure 2:
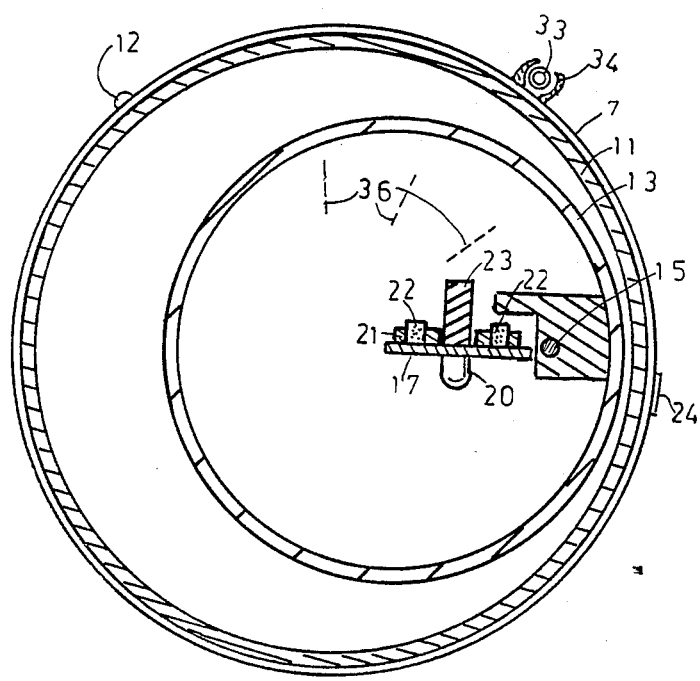
FIG. 2 is a cross sectional view taken through plane 2—2 of FIG. 1.
Figure 3:
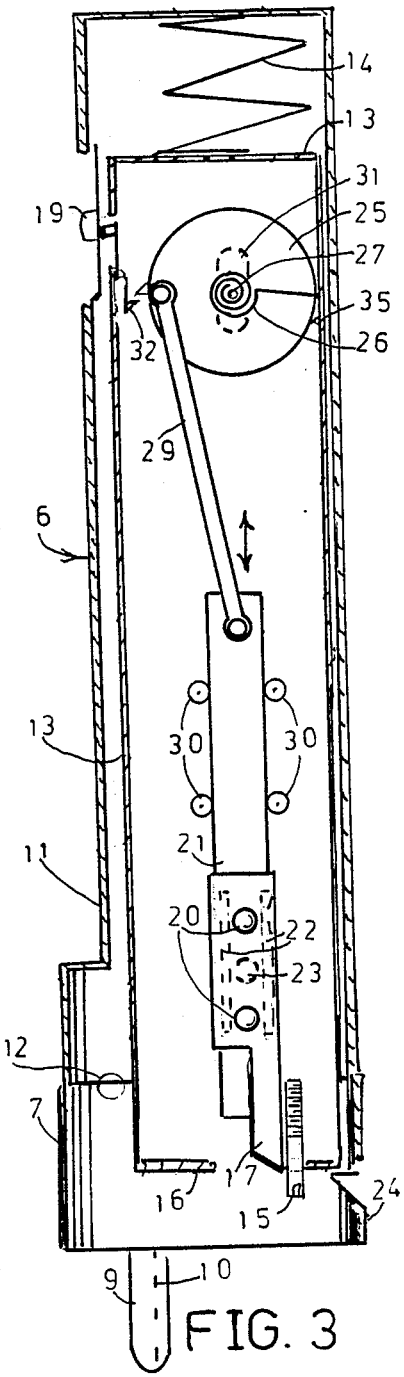
FIG. 3 is a longitudinal section through the device.

FIGS. 2 and 3 show further details of construction. The skin surface sensor 15 may be a small socket head screw that may be adjusted to increase or decrease the effective depth of penetration of the blade 17 in its motion. The blade 17 has two holes in its shank portion that engages two pins 20 fixed to blade holder 21. A pair of permanent magnets 22 mounted on blade holder 21 hold the blade 17 in place after it is slipped onto the two pins so that installing a fresh blade is very easy. A push pin 23 mounted on holder 21 opposite to pins 20 is pushed in to force a used blade away from the magnets 22 and off holding pins 20 to discard a used blade without touching it. A spring catch 24 limits the downward motion of lancet assembly 13 within the assembly carrier 11. To change blades, the catch 24 is pressed with the device 6 held vertically and the assembly will move out far enough to expose the blade carrier to permit changing the blade. After a new blade is installed, the assembly 13 may be retracted into carrier 11 by inverting it and striking the end against a hard surface. The blade advancing and retracting mechanism includes a rotary wheel 25 connected to a spiral spring 26 that is always partially wound. The wheel 25 rotates on axle 27 affixed to the lancet assembly 13, a connecting rod 29 connects the outer edge of wheel 25 to the blade carrier 21, which is restricted to axial movement by rollers 30. A winding handle 31 on the opposite side of wheel 25 (shown in phantom in FIG. 3) is turned through 180 degrees to increase spring tension and springy catch 32 holds the wheel in this cocked position until pushbutton 19 is pressed to release it. Rotation is stopped at stop 35 after 180 degrees of rotation. Note that axial movement of lancet assembly 13 within assembly carrier 11 doesn't affect the pushbutton operation.

A glass capillary tube 33 with an exact inside diameter and length is snapped into spring fingers 34 mounted on the side of assembly carrier 11. It is available in this convenient location for aspirating by capillarity the exact volume of blood necessary to fill it. The capillary dimensions are selected to provide the exact volume of blood required for the measurement. This ensures optimum test conditions and avoids trying to get more blood than is necessary.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A device for puncturing the skin for blood sampling with a blade, comprising: a) blade holder means for holding said blade in said device; b) blade moving means connected to said blade holder means for rapidly moving said blade holder with said blade exclusively in a rectilinear motion in a first or puncturing direction motion immediately followed by a second or retracting direction motion for rapid puncturing and retraction to minimize pain; c) said blade moving means including a rotary to translatory motion conversion means including a rotary driving element, whereby said rotary driving element, while moving in a single continuous motion in one direction, moves said blade holder through said first and then said second direction motions.

2. The device according to claim 1, including spring means for biasing said rotary driving element to drive said moving means, said spring means providing spring bias to said rotary driving element.

3. The device according to claim 2, in which said blade holder means includes means for removably holding said blade.

4. The device according to claim 1, in which said blade holder means includes means for removably holding said blade.

5. A device for puncturing the skin of the finger for blood sampling with a replaceable blade, comprising:
    (a) finger engaging means for engaging said finger in a reproducible orientation to control the location of said puncturing;
    (b) positioning means attached to said finger engaging means for positioning said finger engaging means at a fixed orientation to a landmark on said finger;
    (c) blade holder means for removably holding said blade in said device;
    (d) blade moving means connected to said blade holder means for rapidly moving said blade holder with said blade downward in a first or puncturing direction immediately followed by an upward or retracting direction motion for rapid puncturing and rectraction to minimize pain;
    (e) lancet assembly means containing said blade holder, and said blade moving means;
    (f) lancet assembly carrier means movably connected to said finger engaging means by indexable means to move said blade to a plurality of exact indexed positions relative to said finger, said lancet assembly means mounted within said lancet carrier means in axially moving condition;
    (g) skin surface sensing means attached to said lancet assembly means and adapted to engage said skin and position said assembly means axially within said carrier means a fixed distance above said skin to control the depth of said puncturing.

6. The device according to claim 5, in which said blade moving means includes a spring.

7. The device according to claim 6, in which said moving means includes a rotary to translatory motion conversion means.

8. The device according to claim 5, including capillary holding means for removably holding a disposable capillary for collecting a fixed volume of blood.

9. The device according to claim 5, including spring bias means for urging said lancet assembly means toward said skin.

10. The device according to claim 5, in which said blade holder means includes magnet means for easier blade changing.

11. A device for puncturing the skin comprising
    (a) skin puncturing means;
    (b) mounting means for mounting said skin puncturing means exclusively for translational, rectilinear motion in a predetermined direction between a retracted position in which said skin puncturing means is in a non-skin puncturing location and an extended position in which said skin puncturing means can affect said puncturing of said skin; and
    (c) actuation means for actuating said translational rectilinear motion of said mounting means, said actuation means including drive means movable over a predetermined path between a first end position, an intermediate position, and a second end position, and connection means for connecting said drive means to said mounting means; said drive means, said predetermined path, and said connection means being so arranged that as said drive means moves from said first end position through said intermediate position to said second end position in a continuous motion in one direction said mounting means moves said skin puncturing means from said retracted position when said drive means is in said first end position, to said extended position when said drive means is in said intermediate position, to said retracted position when said drive means is in said second end position, thereby rapidly and continuously moving said skin puncturing means through said extended position for puncturing said skin in order to minimize the pain created thereby.

12. The device of claim 11, including a housing that encloses said mounting means and said actuation means said housing extending longitudinally in said predetermined direction and said housing including an aperture, whereby said skin puncturing means extends through said aperture in said housing when in said extended position and is contained within said housing when in said retracted position.

13. The device of claim 12 wherein said housing includes a first portion and a second portion, said second housing portion being longitudinally displaceable from and relatively rotatably displaceable with respect to said first housing portion in a plane transverse to said predetermined direction, and wherein said skin puncturing means is affixed to said second housing portion.

14. The device of claim 13 wherein said first housing portion includes body part engaging means for mounting said device relative to a predetermined location with respect to a body part, whereby upon said rotation of said second housing portion with respect to said first housing portion said skin puncturing means can be aligned with different sites on said body part while said first housing portion remains stationary.

15. The device of claim 13 wherein said first portion of said housing includes locator means for locating said first portion of said housing with respect to a predetermined location on said skin where said puncture is desired.

16. The device of claim 12 wherein said housing includes an internal housing portion and an external housing portion, said mounting means being mounted within said internal housing portion.

17. The device of claim 16 wherein said internal housing portion is relatively longitudinally displaceable within said external housing portion.

18. The device of claim 17 including skin surface sensor means extending from said internal housing portion adapted to engage said skin whereby said internal housing portion can be longitudinally located within said external housing portion at a predetermined location such that said skin puncturing means will extend from said housing to puncture said skin by a predetermined depth when in said extended position.

19. The device of claim 17 including spring bias means for biasing said internal housing portion relative to said external housing portion so as to urge said internal housing portion towards said housing aperture.

20. The device of claim 11 wherein said drive means includes a rotary member.

21. The device of claim 20 wherein said drive means includes spring means for biasing said rotary member from said first end position towards said second end position, and catch means for maintaining said rotary member in said first end position.

22. The device of claim 21 wherein said actuation means includes release means for releasing said catch means whereby said spring means can drive said rotary member from said first end position towards said second end position.

23. The device of claim 21 wherein said drive means includes rewind means for returning said rotary member from said second end position to said first end position against said bias of said spring means.

24. The device of claim 11 wherein said skin puncturing means comprises a blade.

25. The device of claim 11 wherein said mounting means includes skin puncturing means holding means.

26. The device of claim 25 wherein said skin puncturing means comprises metal, and including magnet means mounted on said skin puncturing means holding means for releasably mounting said skin puncturing means thereon.

27. The device of claim 25 including pin means extending from said skin puncturing means holding means, and wherein said skin puncturing means includes aperture means corresponding to said pin means for releasably mounting said skin puncturing means on said skin puncturing means holding means by inserting said pin means into said aperture means.

28. The device of claim 11 including capillary holding means for removably holding a disposable capillary holding tube for collecting a fixed volume of blood upon said puncturing of said skin.

29. A device for puncturing the skin comprising:
(a) skin puncturing means;
(b) mounting means for mounting said skin puncturing means for translational motion in a predetermined direction between a retracted position in which said puncturing means is in a non-skin puncturing location and an extended position in which said skin puncturing means can effect said puncturing of said skin;
(c) actuation means for actuating said translational motion of said mounting means; and
(d) a housing extending longitudinally in said predetermined direction and including an aperture, said mounting means and said actuation means being mounted within said housing such that said skin puncturing means extends from said aperture in said housing when in said extended position and is contained within said housing when in said retracted position, said housing including a first portion and a second portion, said second housing portion being longitudinally displaced from and relatively rotatable with respect to said first housing portion in a plane transverse to said predetermined direction, said skin puncturing means being affixed to said second housing portion, said first housing portion including body part engaging means for mounting said device relative to a predetermined location with respect to a body part, whereby upon said rotation of said second housing portion with respect to said first housing portion said skin puncturing means can be aligned with different sites on said body part while said first housing portion remains stationary.

30. The device of claim 29 wherein said second housing portion includes an internal housing portion and an external housing portion, said mounting means and said actuation means being mounted within said internal housing portion.

31. The device of claim 30 wherein said internal housing portion is relatively longitudinally displaceable with respect to said external housing portion.

32. The device of claim 29 wherein said actuation means includes drive means movable over a predetermined path between a first end position, an intermediate position, and a second end position, and connection means for connecting said drive means to said mounting means; said drive means, said predetermined path, and said connection means being so arranged that as said drive means moves from said first end position through said intermediate position to said second end position said mounting means moves said skin puncturing means from said retracted position when said drive means is in said first end position, to said extended position when said drive means is in said intermediate position, to said retracted position when said drive means is in said second end position, thereby rapidly and continuously moving said skin puncturing means through said extended position for puncturing said skin in order to minimize the pain created thereby.

33. The device of claim 32 wherein said drive means includes a rotary member.

34. The device of claim 33 wherein said drive means includes spring means for biasing said rotary member from said first end position towards said second end position, and catch means for maintaining said rotary member in said first end position.

35. The device of claim 34 wherein said actuation means includes release means for releasing said catch means whereby said spring means can drive said rotary member from said first end position to said second end position.

36. The device of claim 34 wherein said drive means includes rewind means for returning said rotary member from said second end position to said first end position against said bias of said spring means.

37. A device for puncturing the skin comprising:
   (a) skin puncturing means;
   (b) mounting means for mounting said skin puncturing means for translational rectilinear motion in a predetermined direction between a retracted position in which said skin puncturing means is in a non-skin puncturing location and an extended position in which said skin puncturing means can affect said puncturing of said skin;
   (c) actuation means for actuating said translational rectilinear motion of said mounting means;
   (d) a housing extending longitudinally in said predetermined direction, and including an aperture, said mounting means and said actuation means being mounted within said housing such that said skin puncturing means extends from said aperture in said housing when in said extended position and is contained within said housing when in said retracted position, said housing including an internal housing portion and an external housing portion, said mounting means and said actuation means being mounted within said internal housing portion, said internal housing portion being entirely enclosed within said external housing portion and relatively longitudinally displaceable within said external housing portion independent of said translational motion of said skin puncturing means; and
   (e) skin sensor means extending from said internal housing portion for engaging said skin whereby said internal housing portion can be and for longitudinally locating said internal housing portion within said external housing portion at a predetermined distance from the skin that will not change during said puncturing such that said skin puncturing means will extend from said housing to puncture said skin by a predetermined depth when in said extended position.

38. The device of claim 37 including spring bias means for biasing said internal housing portion relative to said external housing portion so as to urge said internal housing portion towards said housing aperture.

39. The device of claim 37 including limit means for limiting said longitudinal displacement of said internal housing portion with respect to said external housing portion.

40. The device of claim 37 wherein said external housing portion includes a first external housing portion and a second external housing portion, said second external housing portion being relatively rotatable with respect to said first external housing portion in a plane transverse to said predetermined direction.

41. The device of claim 40 wherein said second external housing portion includes body part engaging means for mounting said device relative to a predetermined location with respect to a body part, whereby upon said rotation of said second external housing portion with respect to said first external housing portion said skin puncturing means can be aligned with different sites on a body part while said first external housing portion remains stationary.

* * * * *